United States Patent [19]  [11]  4,158,057
Stanko  [45]  Jun. 12, 1979

[54] PREVENTION OF THE ACCUMULATION OF FATTY DEPOSITS IN THE LIVER

[76] Inventor: Ronald T. Stanko, 596 Dorseyville Rd., Pittsburgh, Pa. 15238

[21] Appl. No.: 562,815

[22] Filed: Mar. 28, 1975

[51] Int. Cl.² .................. A61K 31/525; A61K 31/19; A61K 31/12
[52] U.S. Cl. .................................... 424/252; 424/317; 424/331
[58] Field of Search ......................... 424/252, 317, 331

[56] References Cited
PUBLICATIONS

Chemical Abstracts 67:19055b, (1967).
Chemical Abstracts 71:121284v, (1969).
Chemical Abstracts 72:19554s, (1920).

Primary Examiner—Leonard Schenkman
Attorney, Agent, or Firm—Thomas H. Murray

[57] ABSTRACT

A method is provided for preventing the accumulation of fatty deposits in mammalian livers due to ingestion of alcohol. The method consists of administering a suitable dosage of a mixture of pyruvate and dihydroxyacetone to which riboflavin may also be added.

8 Claims, 1 Drawing Figure

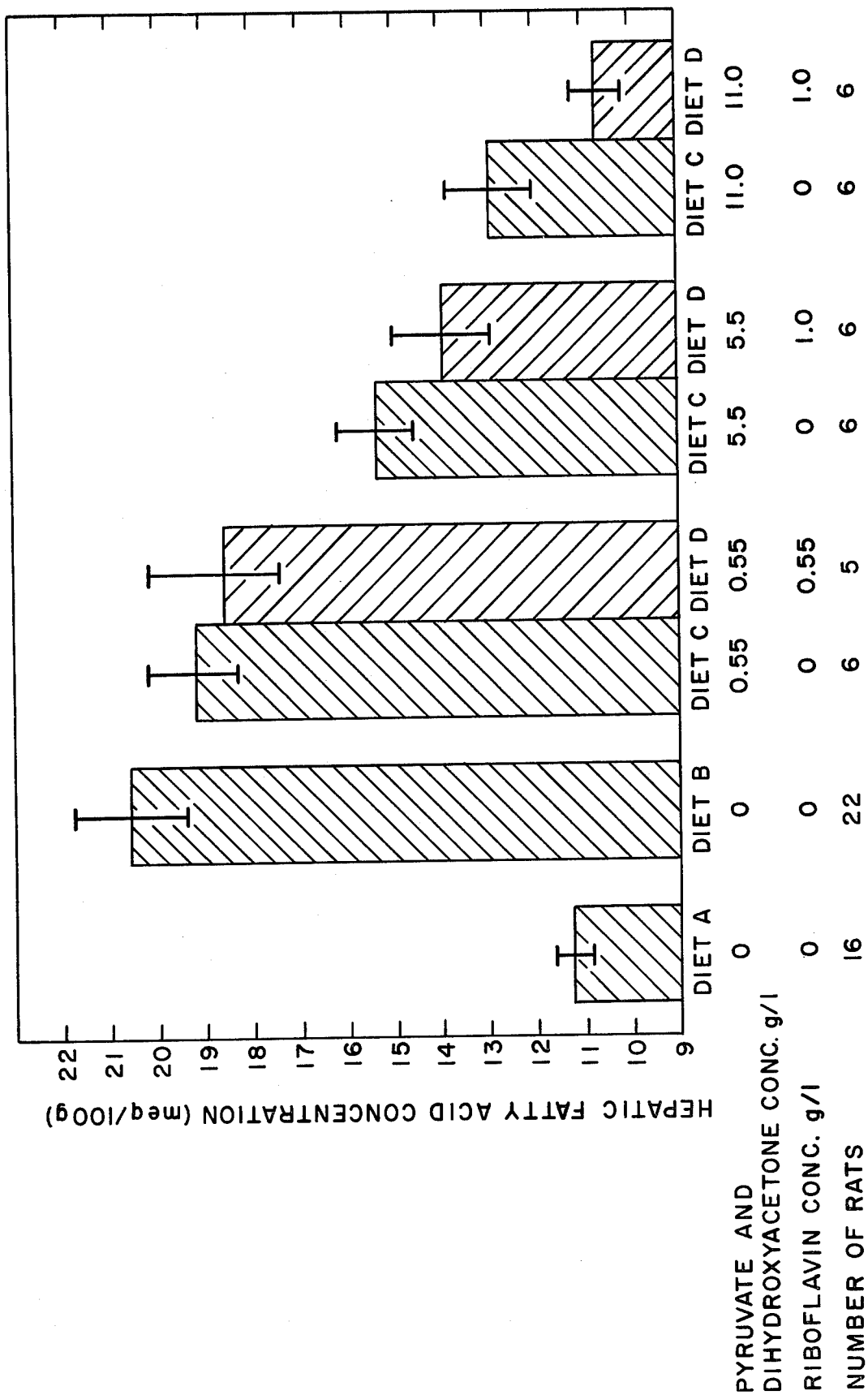

PREVENTION OF THE ACCUMULATION OF FATTY DEPOSITS IN THE LIVER

BACKGROUND OF THE INVENTION

The present invention relates, in general, to the prevention of fatty deposits in mammalian livers. It is well known that one of the consequences of the ingestion of ethyl alcohol in mammals, including man, is the accumulation of fatty deposits in the liver. Such accumulation tends to become irreversible in many cases, and may have serious consequences, so that prevention or reduction of these deposits protects the liver against one of the effects of alcohol.

Attempts have been made to find a suitable chemical agent which would be effective in preventing fatty deposits from accumulating in the liver, but satisfactory results have not been obtained. These prior attempts have not resulted in developing a satisfactory chemical agent because of such problems as blunting of the lipotropic effect if more than one dose of alcohol is ingested, or if the proportion of dietary fat content is high as that usually consumed in the diet of higher animals and man.

SUMMARY OF THE INVENTION

In accordance with the present invention, it has been found that these undesirable fatty liver deposits can be prevented by administering a mixture of pyruvate and dihydroxyacetone in suitable amounts. These substances are naturally occurring metabolic products which are normally present in the body. The effectiveness of the mixture may be somewhat increased by the addition of a suitable amount of riboflavin. Studies on rats have shown that this mixture is highly effective when administered in proper quantities, although the exact dosage is not critical, and the fatty acid content of the liver is held to normal levels even with a diet having a very high content of alcohol and fat.

BRIEF DESCRIPTION OF THE DRAWING

The single FIGURE of the drawing is a chart illustrating the results of experimental studies on rats.

DESCRIPTION OF THE PREFERRED EMBODIMENTS

As previously indicated, the invention is directed to the prevention of the accumulation of fatty deposits in the livers of mammals. One approach to this problem would involve the selection of a lipotropic agent on the basis of a consideration of the products of alcohol metabolism in the body. Oxidation of alcohol results in the production of an excessive amount of hydrogen ions in the body, and this increased acidity results in decreases in the concentrations of the oxidized forms of certain intermediary substrates and cofactors necessary for effective oxidative metabolism. This situation favors the synthesis of lipids or fatty acids, and reduces the oxidation of fatty acids. A series of tests, described below, was intended to determine whether oral administration of naturally occurring chemical agents known to be hydrogen acceptors, or to be necessary for efficient oxidative metabolism, would be effective in protecting the liver against the fat-accumulating effect of alcohol.

In this series of tests, these groups of male rats weighing 240 to 270 grams were used, and were fed a standard low-fat laboratory diet containing 4.5% fat, 23% protein and 57.5% carbohydrate for ten days. In addition to this diet, the first or control group of rats received each morning 1.5 milliliters of water per 100 grams of body weight, the second group received 1.5 milliliters of 47.5% ethanol per 100 grams of body weight, and the third group received the same amount of alcohol as the second group and in addition received one of the agents, or combinations of agents, listed in Table I at the rate of 6.6 milligrams of the agent per 100 grams of body weight. On the eleventh day, the rats were sacrificed, the livers removed, rinsed in ice-cold saline solution, and the total fatty acid content of the liver of each rat was determined. The results of these tests are shown in Table I which shows the average fatty acid concentration in the livers of each group, the number of rats in each group being shown in parentheses.

Table I

Effect of Chemical Agents on Hepatic Fat Accumulation

| | Fatty Acid Concentration (meq/100 g liver) |
|---|---|
| Control (Group 1) | 9.74 ± 0.28 (30) |
| Ethanol (Group 2) | 11.35 ± 0.36 (23) |
| Chemical Agents used in Ethanol-treated Rats: (Group 3) | |
| a. Cysteine | 12.67 ± 1.67 (6) |
| b. Dihydroascorbic acid | 12.15 ± 1.92 (6) |
| c. Glutathione | 11.46 ± 1.28 (6) |
| d. Niacin | 11.35 ± 0.81 (5) |
| e. Pyruvate | 11.00 ± 0.62 (11) |
| f. Dihydroxyacetone | 10.98 ± 0.70 (10) |
| g. Riboflavin | 9.89 ± 0.48 (13) |
| h. Dihydroxyacetone + thiamine | 11.13 ± 0.46 (6) |
| i. Pyruvate + thiamine | 11.00 ± 0.83 (6) |
| j. Pyruvate + dihydroxyacetone | 9.79 ± 0.56 (12) |
| k. Cysteine + dihydroascorbic acid + niacin | 14.56 ± 1.19 (6) |
| l. Pyruvate + niacin + dihydroascorbic acid | 10.81 ± 0.42 (6) |
| m. Pyruvate + riboflavin + thiamine | 10.65 ± 0.70 (11) |
| n. Riboflavin + dihydroxyacetone + thiamine | 10.21 ± 0.56 (10) |
| o. Pyruvate + dihydroxyacetone + riboflavin | 9.18 ± 0.39 (13) |
| p. Pyruvate + dihydroxyacetone + riboflavin + thiamine | 9.56 ± 0.27 (15) |

The effect of the alcohol fed to the second group of rats is readily apparent in the significantly higher concentration of fatty acids in the livers of these rats as compared to the control group. The third group of rats shows the effect on the fatty acid concentration of treatment with the various chemical agents and combinations of agents shown. It will be seen that none of the chemical agents used alone and shown in lines a-f of the Table had any significant effect on the fat concentration in the liver. Riboflavin (line g), however, significantly reduced the fatty acid content. The remaining lines of the Table show the effects of various combinations of chemical agents. The combination of pyruvate and dihydroxyacetone (line j) significantly reduced the fatty acid concentration to a level approximately equal to that of the control group. The addition of riboflavin to this mixture (line o) further increased the effectiveness, the riboflavin appearing to potentiate the effect of pyruvate and dihydroxyacetone by making the effect more consistent and statistically more significant. Mixtures of other agents shown in the Table had no effect on the fatty acid concentration, and the addition of thiamine to the pyruvate-dihydroxyacetone-riboflavin mixture (line p) had no significant effect. It appears, therefore, that the various chemical agents other than riboflavin listed in Table I are not effective individually. The pyruvate and dihydroxyacetone are equally ineffective when used alone, but when used in combination, the mixture of these two agents produces a marked reduction in the fatty acid concentration, the addition of riboflavin to the mixture further enhancing the effect. No other mixtures of any of the substances listed had any significant effect on the fatty acid concentration.

Pyruvate (pyruvic acid-$CH_3COCOOH$) is a product of the metabolism of glucose and some amino acids, while dihydroxyacetone (($CH_2OH)_2CO$) is a product of the metabolism of fatty acids and certain amino acids. These substances are, therefore, both natural metabolites which are normally present in the body, while riboflavin (Vitamin B2) is also present in the body. All of these substances, therefore, are natural products which are normally harmless.

Since the tests summarized in Table I were made with a relatively low-fat diet, additional studies were made using a diet with a much higher fat content, the results being shown in the accompanying chart. In these studies, male rats weighing 150 to 175 grams were fed for ten days on one of the following diets:

Diet A—A standard laboratory liquid diet containing ;b 35% fat, 18% protein and 47% carbohydrate.

Diet B—Similar to Diet A with partial isocaloric substitution of carbohydrate by 95% ethanol (67 milliliters per 1000 milliliters of Diet A). This resulted in a composition of 35% fat, 18% protein, 10% carbohydrate, and 37% alcohol.

Diet C—Diet B with the addition of varying amounts of a mixture of pyruvate and dihydroxyacetone in approximately equal parts.

Diet D—Diet C with the addition of varying amounts of riboflavin.

After ten days, the rats were sacrificed and the fatty acid content of the livers was determined as before. The results are shown in the drawing in the form of a bar chart, showing the average fatty acid concentration of each of the several groups of rats, as well as the range of individual values. The rats which were fed only Diet A, which was the control group, had a relatively low average concentration of fatty acid, while the group fed on Diet B with a large alcohol content had a greatly increased concentration of fatty acid in the livers. The remaining groups of rats, fed on Diets C and D with increasing amounts of the pyruvate and dihydroxyacetone mixture, as shown on the chart in grams per liter of liquid diet, showed progressively lower concentrations of fatty acid. In each group, the addition of an amount of riboflavin (Diet D) appeared to potentiate the effect as noted before. It will be noted that the fatty acid concentration in the liver decreased with increasing amounts of the pyruvate-dihydroxyacetone mixture and at the maximum dosage used the concentration is comparable to that of the control group. With the addition of riboflavin the concentration was actually lower than that of the control group.

It will be apparent that a mixture of pyruvate and dihydroxyacetone, or of pyruvate, dihydroxyacetone and riboflavin, is effective in reducing or substantially preventing the accumulation of fatty deposits in mammalian livers. The effect is dependent on the dosage, as shown in the chart, but the maximum dosage used in the studies discussed above of 11 grams per liter of daily diet intake reduced the fatty acid concentration to or below that of the control group which received no alcohol at all. It would appear, therefore, that a dosage of this order of magnitude is the maximum necessary for full effectiveness, and that a higher dosage would have no significantly increased effect. Since the pyruvate and dihydroxyacetone are both natural metabolites which are normally present in the body in some concentration, they are harmless to the organism, at least in the quantities here discussed, and a considerably greater dosage than that indicated would have no harmful effects. The pyruvate and dihydroxyacetone are preferably present in the mixture in approximately equal parts, although the proportion does not appear to be critical, and the riboflavin, if used, may be in lesser quantity although the proportion is not critical. A highly effective treatment is thus provided for preventing accumulaton of fatty deposits in the livers of mammals. The pyruvate and dihydroxyacetone, which individually have no effect, when used in combination produce the very marked reduction in fatty acid concentration discussed above which may be somewhat enhanced by the further addition of riboflavin. An effective treatment is thus provided utilizing natural metabolites which are normally present in the body, and which are readily available at relatively low cost.

I claim as my invention:

1. A method of preventing excessive accumulation of fatty deposits in the liver of a mammal due to ingestion of ethanol which comprises administering orally to said mammal a therapeutic mixture of effective amounts of pyruvate and dihydroxyacetone.

2. The method of claim 1 in which said mixture also includes riboflavin.

3. The method of claim 1 in which said mixture contains substantially equal parts of pyruvate and dihydroxyacetone.

4. The method of claim 1 in which said mixture is administered in an amount of the order of eleven grams per liter of dietary intake of the mammal.

5. A therapeutic composition for oral administration for prevention of excessive accumulation of fatty deposits in mammalian livers due to ingestion of ethanol, said composition comprising a mixture of effective amounts of pyruvate and dihydroxyacetone.

6. The composition of claim 5 including riboflavin as an additional constituent.

7. The composition of claim 5 in which the pyruvate and dihydroxyacetone are present in substantially equal parts.

8. The composition of claim 7 and including riboflavin as an additional constituent.

* * * * *